(12) United States Patent
Lu

(10) Patent No.: US 7,624,968 B2
(45) Date of Patent: Dec. 1, 2009

(54) COMPRESSOR NEBULIZER WITH A PRESSURE GAGE

(76) Inventor: Hsueh-Yu Lu, 5F-23, 70, Fu-Shing Road, Taoyuan (TW)

( * ) Notice: Subject to any disclaimer, the term of this patent is extended or adjusted under 35 U.S.C. 154(b) by 132 days.

(21) Appl. No.: 12/071,657

(22) Filed: Feb. 25, 2008

(65) Prior Publication Data
US 2009/0211571 A1 Aug. 27, 2009

(51) Int. Cl.
*B01F 3/04* (2006.01)
*A61M 11/02* (2006.01)

(52) U.S. Cl. .................... 261/30; 128/200.18; 239/338; 261/78.2

(58) Field of Classification Search .................... 261/26, 261/30, 78.2, DIG. 65; 239/338; 128/200.18
See application file for complete search history.

(56) References Cited

U.S. PATENT DOCUMENTS

| | | | | |
|---|---|---|---|---|
| 2,906,513 | A * | 9/1959 | Tabor | 261/78.2 |
| 3,301,255 | A * | 1/1967 | Thompson | 128/200.18 |
| 3,379,194 | A * | 4/1968 | Ziermann | 128/200.21 |
| 3,630,196 | A * | 12/1971 | Bird et al. | 128/200.18 |
| 3,940,064 | A * | 2/1976 | Takaoka | 239/74 |
| 4,200,093 | A * | 4/1980 | Camp | 128/200.14 |
| 4,427,004 | A * | 1/1984 | Miller | 128/200.21 |
| 4,951,659 | A * | 8/1990 | Weiler et al. | 128/200.18 |
| 5,193,354 | A * | 3/1993 | Kleinberger et al. | 62/247 |
| 5,655,520 | A * | 8/1997 | Howe et al. | 128/203.12 |
| 5,687,912 | A * | 11/1997 | Denyer | 239/343 |
| 5,823,179 | A * | 10/1998 | Grychowski et al. | 128/200.18 |
| 5,889,201 | A * | 3/1999 | Turchin et al. | 73/53.01 |
| 6,644,304 | B2 * | 11/2003 | Grychowski et al. | 128/200.18 |
| 6,736,135 | B1 * | 5/2004 | Klich | 128/200.14 |
| 6,748,945 | B2 * | 6/2004 | Grychowski et al. | 128/200.21 |
| 7,051,736 | B2 * | 5/2006 | Banner et al. | 128/204.21 |
| 7,341,056 | B1 * | 3/2008 | Tucker | 128/200.14 |
| 7,568,480 | B2 * | 8/2009 | Foley et al. | 128/200.14 |
| 2007/0227536 | A1 * | 10/2007 | Rivera et al. | 128/200.21 |

FOREIGN PATENT DOCUMENTS

EP 111163 A2 * 6/1984
EP 441643 A1 * 8/1991

* cited by examiner

*Primary Examiner*—Richard L Chiesa

(57) ABSTRACT

For changing a liquid medicine into a fine mist a compressor nebulizer is disclosed to include a pressure gage that indicates the pressure range of the compressed air passing out of the air pump to the nebulizer cup through aerosol tubing so that the user can quickly recognize the normal operation of the device and, if abnormal, decide if external parts should be replaced or the device should be returned for repair.

4 Claims, 5 Drawing Sheets

COMPRESSOR NEBULIZER WITH A PRESSURE GAGE

BACKGROUND OF THE INVENTION

1. Field of the Invention

The present invention relates to a compressor nebulizer for changing a liquid medicine into aerosol mist that can be inhaled through a mouthpiece or mask and more particularly, to a compressor nebulizer that has a pressure gage to indicate the pressure range of the compressed air under supply.

2. Description of the Related Art

Inhalation therapy is the latest approach to the management of inflammatory airway disease. A compressor nebulizer is normally used to administer medication to people in forms of aerosol mist to the airways. It is commonly used in treating cystic fibrosis, asthma, and other respiratory diseases.

A regular compressor nebulizer generally comprises a nebulizer cup for holding a liquid medicine, and an air compressor for providing compressed air to the nebulizer cup through an aerosol tubing to change the liquid medicine into a fine mist for enabling the mist medicine to be deeply inhaled into the airways and lungs of a person by means of a mouthpiece or mask.

After a long use of a compressor nebulizer, the pressure of the compressed air may be excessively low, lowering the therapy effect. In this case, the user may not discover the problem. If there is any trouble at an external part (such as blocking of the nebulizer cup, falling of the plug inside the nebulizer cup, blocking or breaking of the aerosol tubing, etc.), the user may be unable to find out the source of the problem. In this case, the user may reject the product or send the product to the distributor for inspection, wasting much maintenance time and handling cost.

SUMMARY OF THE INVENTION

The present invention has been accomplished under the circumstances in view. It is the main object of the present invention to provide a compressor nebulizer, which indicates the pressure range of the compressed air being supplied, assuring normal functioning of the device. It is another object of the present invention to provide a compressor nebulizer, which gives an under-pressure indication, a normal pressure indication, or an over-pressure indication subject to the compressed air supplying condition during the operation of the device for quick recognition of the operation status of the device. It is still another object of the present invention to provide a compressor nebulizer, which gives a pressure range indication, preventing an improper judgment, reducing the chance of product rejection and handling time and cost, and facilitating maintenance work and troubleshooting.

To achieve these and other objects of the present invention, the compressor nebulizer is provided with a pressure gage. The pressure gage is connected to a connector between the air output side of the air pump and the aerosol tubing of the nebulizer cup for indicating the pressure of the compressed air passing out of the air pump to the nebulizer cup during operation of nebulizer.

The dial face of the pressure gage is divided into an under-pressure indication zone, a normal pressure indication zone, and an over-pressure indication zone. If the pointer indicates the under-pressure indication zone, there may be an air leakage in the internal tubing or the air pump may have a trouble. At this time, the liquid medicine can still be turned into a mist, however the particle size of fine drops of the liquid medicine will be excessively great, providing a poor therapy effect, and a factory inspection is necessary. If there is a problem in use while the pointer of the pressure gage is indicating the normal pressure indication zone, it means a problem in the external parts, such as aerosol tubing problem, falling of the plug inside the nebulizer cup, etc. At this time, the user must check the external parts. If the pointer indicates the over-pressure indication zone, check whether the nebulizer cup is blocked, or the aerosol tubing is twisted or blocked. At this time, a replacement of the nebulizer cup or aerosol tubing may be necessary.

DETAILED DESCRIPTION OF THE PREFERRED EMBODIMENT

Figure 1:
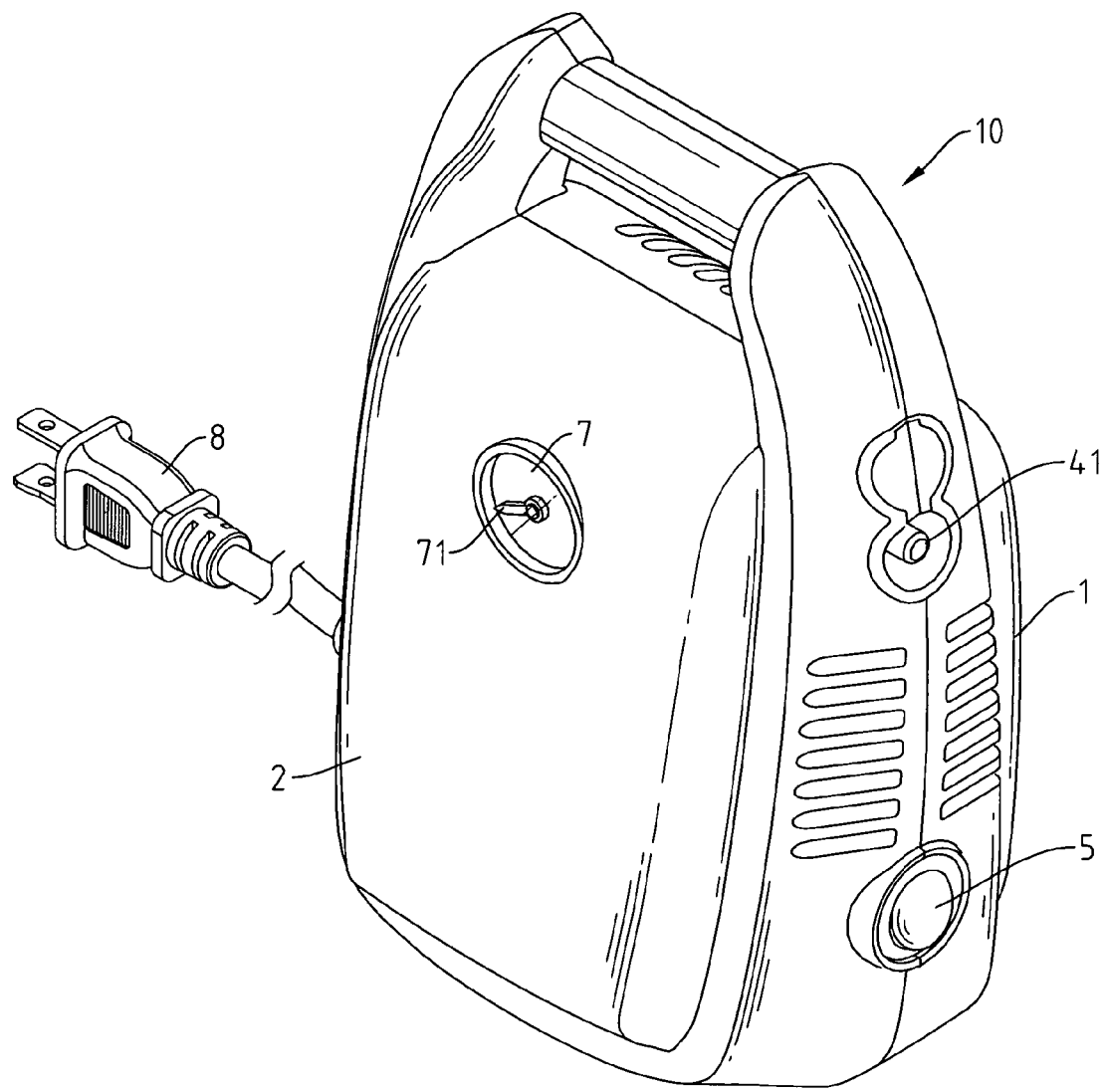
FIG. 1 is an elevational view of a compressor nebulizer in accordance with the present invention.
Figure 2:
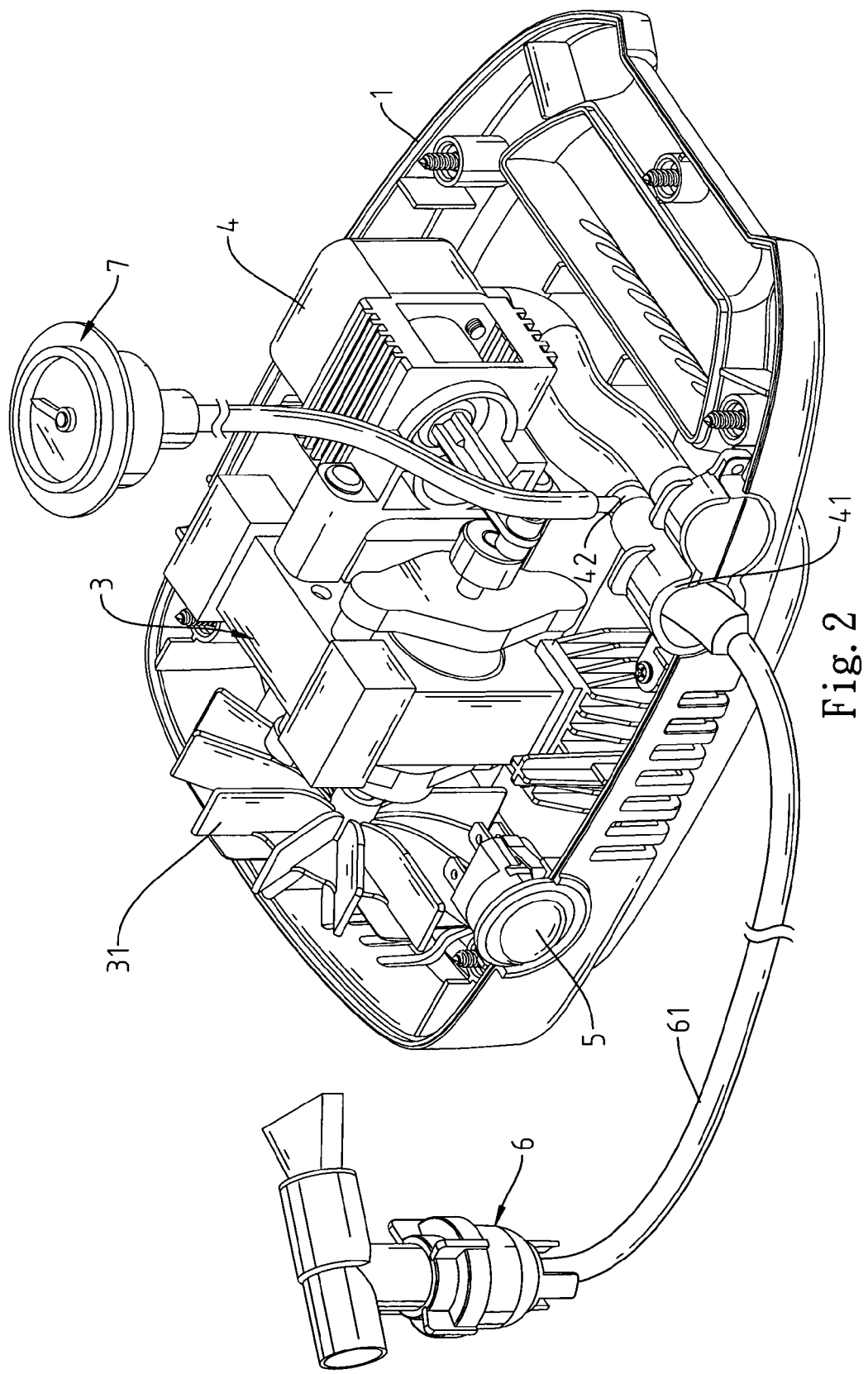
FIG. 2 is an elevational view of the present invention, showing the internal arrangement of the compressor nebulizer.
Figure 5:
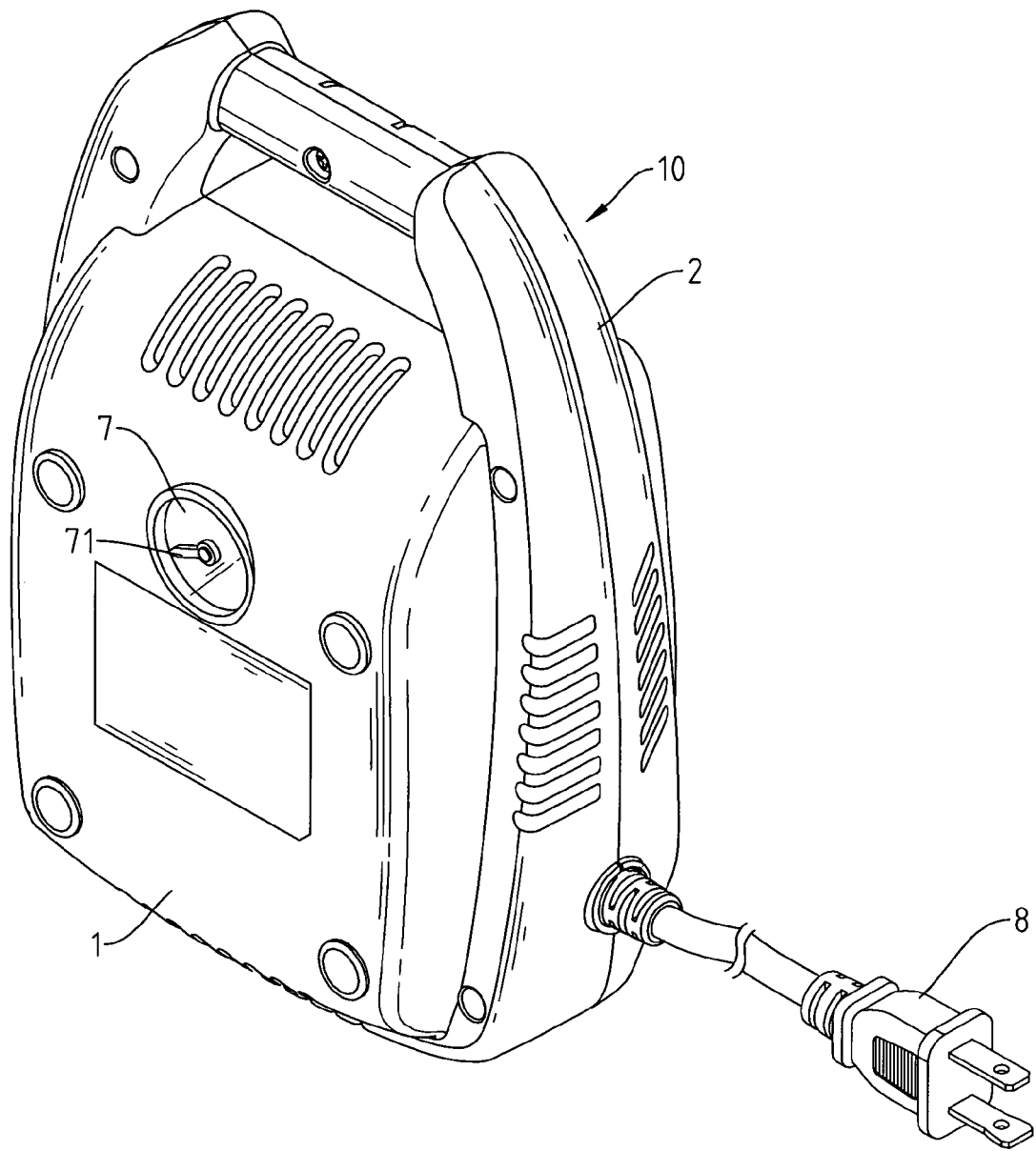
FIG. 5 is an elevational view of an alternate form of the present invention, showing the pressure gage installed in the bottom shell.

Referring to FIGS. 1, 2 and 5, a compressor nebulizer in accordance with the present invention is shown comprising a housing 10, which is formed of a bottom shell 1 and a top cover 2, a motor 3 fixedly mounted inside the bottom shell 1, an air pump 4 fixedly mounted inside the bottom shell 1 and coupled to the motor 3, a fan 31 coupled to the motor 3 inside the bottom cover shell 1 and rotatable with the motor 3 to cause currents of air for dissipation of heat during operation of the motor 3 and the air pump 4, a first connector 41 connected to the air output side of the air pump 4 and extended to the outside of the bottom shell 1, a nebulizer cup 6, which has an aerosol tubing 61 connectable to the first connector 41, a second connector 42 connected to the air output side of the air pump 4, a pressure gage 7 mounted in the housing 10 (either in the bottom shell 1 as shown in FIG. 5, or the top cover 2 as shown in FIG. 2) and connected to the second connector (for example, a T-connector) 42 for indicating the pressure of the compressed air passing out of the air pump 4 to the aerosol tubing 61 and the nebulizer cup 6 during operation of the motor 3 and the air pump 4, a power cable 8 electrically coupled with the motor 3 and connectable to an external power source to provide the motor 3 with the necessary working voltage, and a power switch 5 mounted in the bottom shell 1 and electrically connected between the motor 3 and the power cable 8 and partially extended to the outside of the bottom shell 1 for operation by the user to turn on/off the motor 3. The nebulizer cup 6 holds a liquid medicine. When the user switched on the power switch 5, the motor 3 is started to move the air pump 4 and the fan 31, providing a compressed air to the aerosol tubing 61 and then the nebulizer cup 6, and therefore the liquid medicine is turned into a fine mist for enabling the mist medicine to be deeply inhaled into the airways and lungs of a person.

Figure 3:
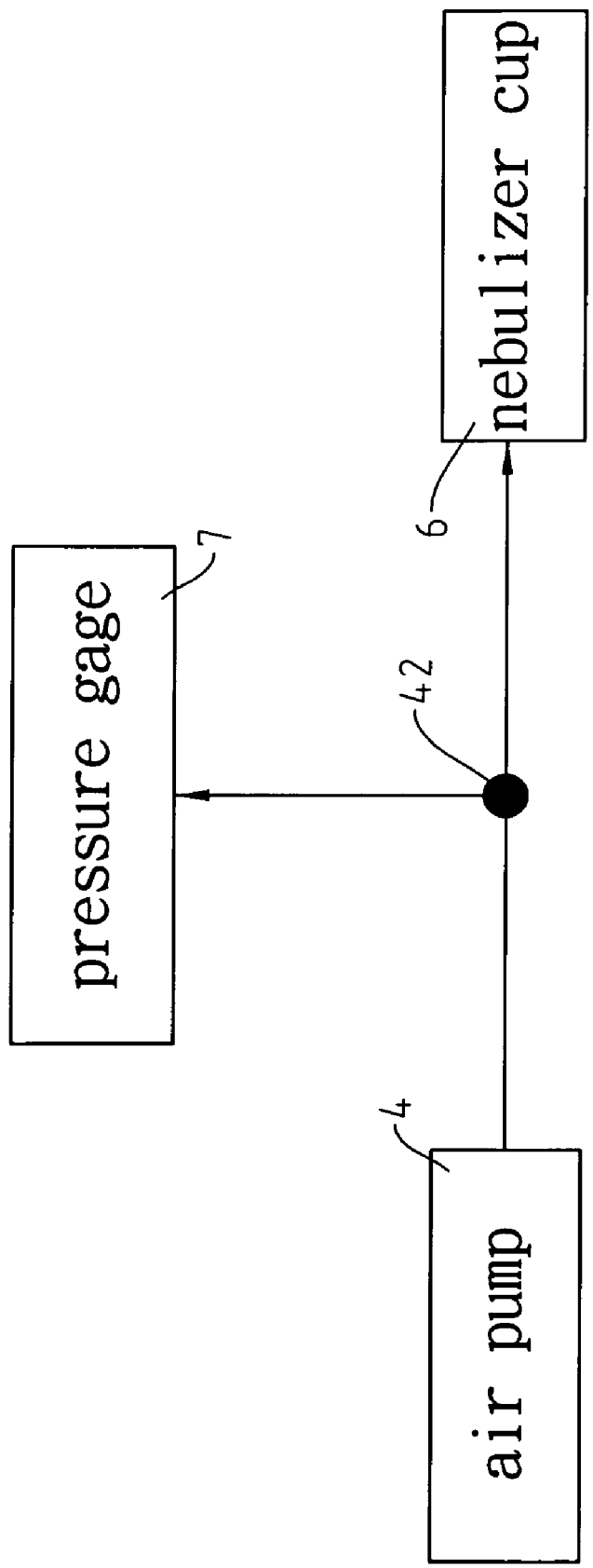
FIG. 3 is a system block diagram of the present invention.
Figure 4:
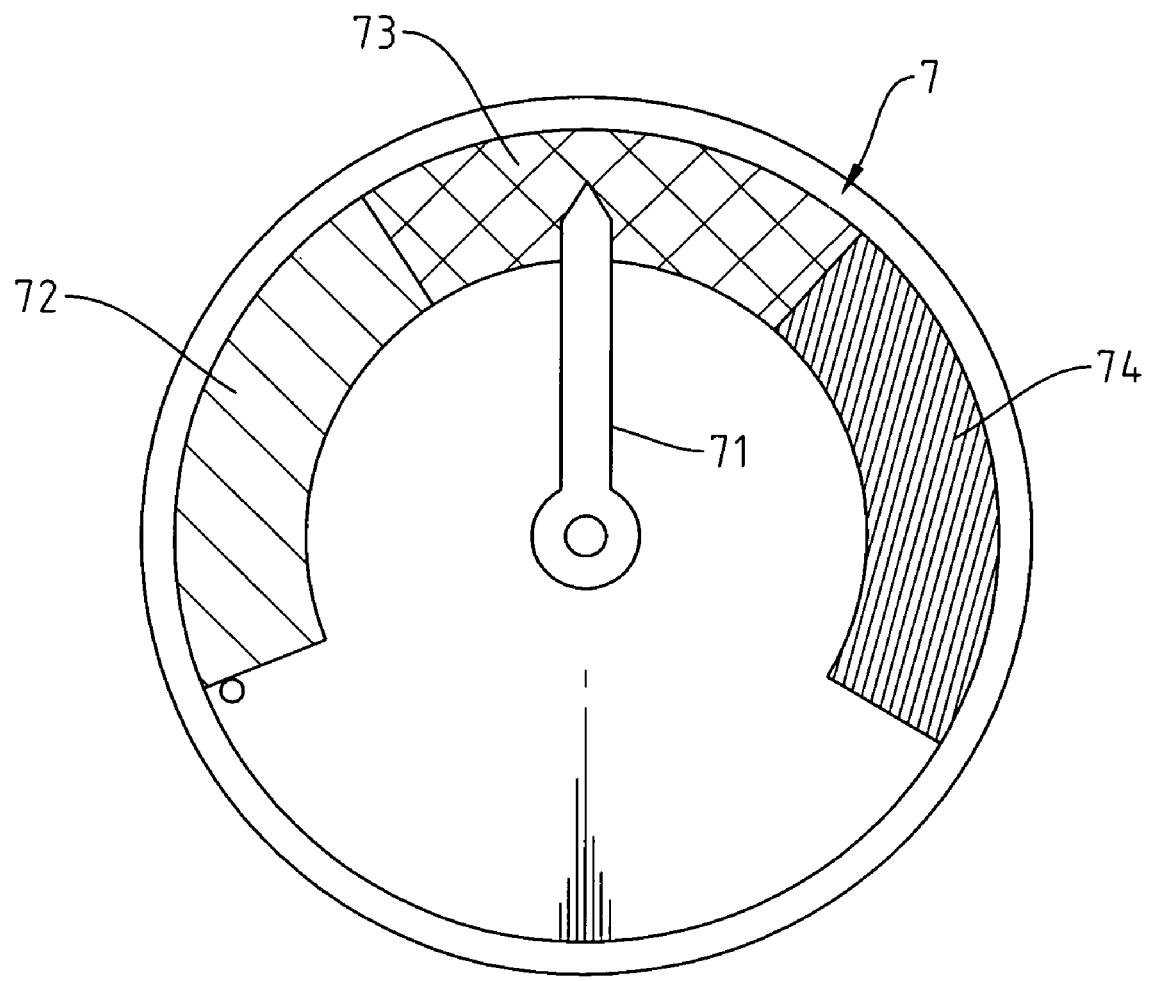
FIG. 4 is a schematic drawing showing a pressure indication of the pressure gage according to the present invention.

Referring to FIGS. 3 and 4 and FIG. 2 again, the pressure gage 7 has its dial face divided into an under-pressure indication zone 72, a normal pressure indication zone 73, and an over-pressure indication zone 74. These pressure indication zones 72~74 may be colored with different colors for quick recognition. The pressure gage 7 has a pointer 71 that is turned relative to the pressure indication zones 72~74 subject to the pressure of the compressed air passing out of the air pump 4 to the aerosol tubing 61 and the nebulizer cup 6 during operation of the motor 3 and the air pump 4. If the pressure of the compressed air is within a predetermined normal range, the pointer 71 indicates the normal pressure indication zone 73. When the pressure of the compressed air surpassed the predetermined normal range, the pointer 71 indicates the over-pressure indication zone 74. When the pressure of the compressed air is below the predetermined normal range, the pointer 71 indicates the under-pressure indication zone 72. If the pointer 71 indicates the under-pressure indication zone 72, there may be an air leakage in the tubing 61 or the air pump 4 may have a trouble. At this time, the liquid medicine can still be turned into a mist; however the particle size of fine drops of the liquid medicine will be excessively great, providing a poor therapy effect. If there is a problem in use while the pointer 71 is indicating the normal pressure indication zone 73, it means a problem in the external parts, such as aerosol tubing problem, falling of the plug of the nebulizer cup, etc. At this time, the user must check the external parts. If the pointer 71 indicates the overpressure indication zone 74, check whether the nebulizer cup 6 is blocked, or the aerosol tubing 61 is twisted or blocked. At this time, a replacement of the nebulizer cup 6 or aerosol tubing 61 may be necessary.

Although a particular embodiment of the invention has been described in detail for purposes of illustration, various modifications and enhancements may be made without departing from the spirit and scope of the invention.

What the invention claimed is:

1. A compressor nebulizer comprising a housing, said housing being formed of a bottom shell and a top cover, an air pump fixedly mounted inside said bottom shell and adapted for producing compressed air, a motor fixedly mounted inside said bottom shell and adapted to drive said air pump, a power cable connectable to an external power source to provide said motor with the necessary working voltage, a power switch mounted in said housing and electrically connected between said motor and said power cable and partially extended to the outside of said housing for operation by the user to turn on/off said motor, a nebulizer cup, said nebulizer cup, and an aerosol tubing connected between said nebulizer cup and said air pump to guide compressed air from said air pump to said nebulizer cup, wherein:

said air pump has a first connector connected to an air output side thereof and extended to the outside of said housing for the connection of said aerosol tubing, and a second connector connected between the air output side of said air pump and said first connector, and a pressure gage connected to said second connector and mounted in said housing for indicating the pressure of the compressed air passing out of said air pump to said aerosol tubing and said nebulizer cup during operation of said motor and said air pump.

2. The compressor nebulizer as claimed in claim 1, wherein said pressure gage has a dial face thereof divided into an under-pressure indication zone, a normal pressure indication zone, an over-pressure indication zone, and a pointer pivoted thereof and turnable relative to said dial face to indicate one of said under-pressure indication zone, said normal pressure indication zone and said over-pressure indication zone subject to the pressure of the compressed air passing out of said air pump to said aerosol tubing.

3. The compressor nebulizer as claimed in claim 1, wherein said pressure gage is mounted in said top cover.

4. The compressor nebulizer as claimed in claim 1, wherein said pressure gage is mounted in said bottom shell.

* * * * *